(12) United States Patent
Bruere et al.

(10) Patent No.: US 10,073,050 B2
(45) Date of Patent: Sep. 11, 2018

(54) ASSEMBLY FOR CAPACITIVE MEASUREMENT OF THE AMOUNT OF GAS IN A FLUID FLOW

(71) Applicants: SAFRAN AIRCRAFT ENGINES, Paris (FR); CAPAAB, Chatenay Malabry (FR)

(72) Inventors: Alain Bruere, Chatenay Malabry (FR); Philippe Nivet, Cantiers (FR); Simon Fammery, La Bonneville sur Iton (FR)

(73) Assignee: Safran Aircraft Engines, Paris (FR)

( * ) Notice: Subject to any disclaimer, the term of this patent is extended or adjusted under 35 U.S.C. 154(b) by 0 days.

(21) Appl. No.: 15/524,950

(22) PCT Filed: Nov. 4, 2015

(86) PCT No.: PCT/FR2015/052981
§ 371 (c)(1),
(2) Date: May 5, 2017

(87) PCT Pub. No.: WO2016/071635
PCT Pub. Date: May 12, 2016

(65) Prior Publication Data
US 2017/0350845 A1    Dec. 7, 2017

(30) Foreign Application Priority Data

Nov. 7, 2014   (FR) ...................... 14 60787

(51) Int. Cl.
*G01R 27/26* (2006.01)
*G01N 27/22* (2006.01)
*G01N 33/22* (2006.01)

(52) U.S. Cl.
CPC ......... *G01N 27/221* (2013.01); *G01N 33/225* (2013.01); *G01N 2027/222* (2013.01)

(58) Field of Classification Search
CPC .. G01N 27/221; G01N 27/222; G01N 27/226; G01N 33/225; G01N 33/2823; G01F 1/64; G01F 1/74; G01F 1/712
See application file for complete search history.

(56) References Cited

U.S. PATENT DOCUMENTS

| 3,374,672 A | 3/1968 | Home |
| 4,751,842 A | 6/1988 | Ekrann et al. |

(Continued)

FOREIGN PATENT DOCUMENTS

| EP | 0488507 A2 | 6/1992 |
| WO | 9403802 | 2/1994 |
| WO | 2013017795 A1 | 2/2013 |

OTHER PUBLICATIONS

International Search Report issued in corresponding International Application No. PCT/FR2015/052981, dated Feb. 9, 2016 (6 pages—English translation included).

*Primary Examiner* — Minh N Tang
(74) *Attorney, Agent, or Firm* — Bookoff McAndrews, PLLC

(57) ABSTRACT

An assembly comprising an upstream pipe, a downstream pipe, and a system (1) for measuring variation in the gas content of a two-phase flow, the assembly including: an insulating sheath (6), an upstream ground (2), a measurement electrode (3), a guard electrode (7), and a downstream ground (4) arranged in succession in the insulating sheath (6) and each presenting an identical internal section defining an internal flow duct for a two-phase flow from the upstream ground (2) towards the downstream ground (4) in line with the upstream pipe and the downstream pipe, the guard electrode (7) being subjected to the same potential as the measurement electrode (3), the measurement electrode (3) measuring the capacitance of the two-phase flow relative to the upstream ground (2) and variation in that capacitance, (Continued)

the upstream ground (2) and the downstream ground (4) being electrically connected to the upstream pipe and to the downstream pipe, respectively.

4 Claims, 2 Drawing Sheets

(56) References Cited

U.S. PATENT DOCUMENTS

| | | | |
|---|---|---|---|
| 6,345,537 B1 * | 2/2002 | Salamitou | G01F 1/64 73/861.04 |
| 6,467,358 B1 | 10/2002 | Nishi et al. | |
| 2007/0186679 A1 | 8/2007 | Zangl et al. | |

* cited by examiner

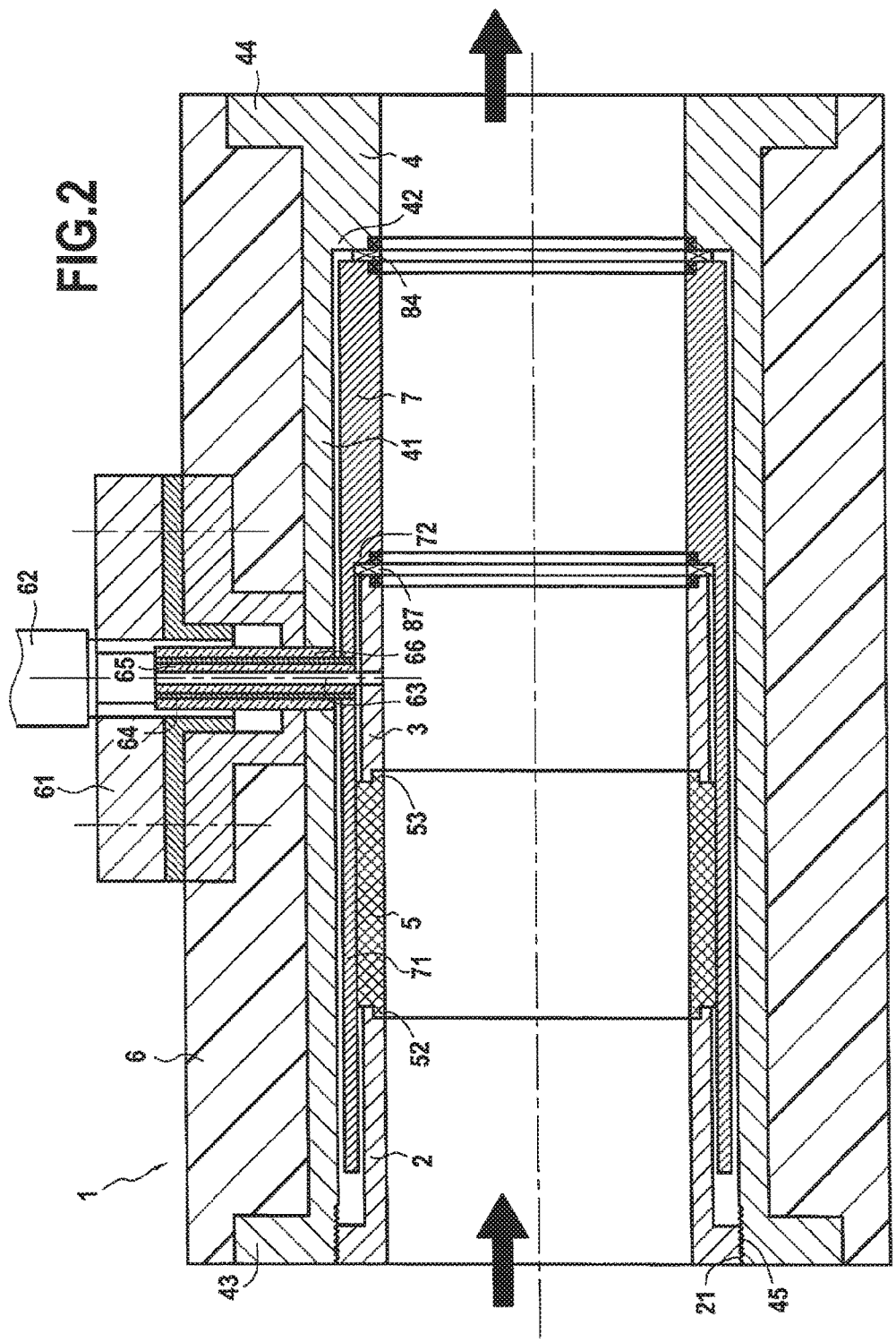

ASSEMBLY FOR CAPACITIVE MEASUREMENT OF THE AMOUNT OF GAS IN A FLUID FLOW

CROSS-REFERENCE TO RELATED APPLICATIONS

This application is the U.S. national phase entry under 35 U.S.C. § 371 of International Application No. PCT/FR2015/052981, filed on Nov. 4, 2015, which claims priority to French Patent Application No. 1460787, filed on Nov. 7, 2014, the entireties of which are herein incorporated by reference.

FIELD OF THE INVENTION

The present description relates to the field of systems for measuring the gas content in a feed pipe.

BACKGROUND

Knowledge of the gas content in an engine feed pipe is a parameter that is important for resetting the operating model applied to the engine as a function of time, in particular for the engines of spacecraft or aircraft, which are typically reset on the basis of experimental data.

Sensors have already been proposed for taking such measurements. Mention may be made in particular of Document WO 2013/017795, which describes such a sensor in detail. The sensor described in that document nevertheless presents several drawbacks.

Firstly, it is a sensor of dimensions that are considerable, having a diameter of about 120 millimeters (mm), which is not suitable for pipes of small dimensions. Furthermore, the sensor described delivers an input signal that is multiplexed, which is penalizing for analyzing results. Finally, the sensor has electrodes and attachment rods positioned within the flow, thereby giving rise to head losses, and is therefore highly penalizing.

Document EP 0 488 507 also describes a sensor for determining the percentage of water in a fluid flow.

That document presents several electrode configurations such that the field that is generated is either parallel or perpendicular to the flow of fluid in the pipe. In particular, that document proposes incorporating a plurality of measurement electrodes in the walls of a fluid flow pipe, each of the electrodes being electrically insulated from the body of the pipe. The system proposed in that document determines the percentage of water in the flow by means of the voltage and the current applied to the electrodes, the voltage measured between the electrodes, and the temperature of the fluid at the measurement point.

Document U.S. Pat. No. 6,467,358 describes a method of measuring the contents of different fluids in a multiphase flow, by means of a system comprising three electrodes arranged in a pipe, with each electrode being electrically insulated from the pipe. That method relies on using a system for measuring electrostatic capacitance or impedance by means of measurements performed via the three electrodes.

The present invention thus seeks to propose a solution that improves these aspects, at least in part.

SUMMARY

To this end, the present invention proposes an assembly comprising an upstream pipe, a downstream pipe, and a system for measuring variation in gas content within a two-phase flow, said system comprising:
an insulating sheath presenting an upstream end and a downstream end; and
an upstream ground, a measurement electrode, a guard electrode, and a downstream ground arranged in succession in said insulating sheath and each presenting an identical internal section defining an internal flow duct for a two-phase flow from the upstream ground towards the downstream ground, the guard electrode being configured so as to be subjected to the same potential as the measurement electrode, the measurement electrode being configured so as to measure the capacitance of the medium constituting the two-phase flow relative to the upstream ground, and to measure variation of that capacitance;
the assembly being characterized in that:
said upstream and downstream pipes present an internal section identical to the internal section of said measurement system;
said upstream and downstream pipes are in fluid flow connection with each other via the measurement system so that the internal duct of the measurement system extends the internal ducts of the upstream and downstream pipes; and
the upstream ground and the downstream ground are electrically connected to the upstream pipe and to the downstream pipe, respectively;
said assembly further comprising a processor unit configured to process the capacitance measurements taken between the measurement electrode and the upstream ground.

There follow various embodiments of this assembly that may be taken singly or in combination.

The assembly may further comprise an insulating spacer arranged in the insulating sheath between the measurement electrode and the upstream ground, the spacer presenting an internal section identical to that of the measurement electrode and of the upstream ground so as to insulate the upstream ground electrically from the measurement electrode.

The guard electrode may comprise a guard sheath having a cylindrical portion extending to the upstream ground between the insulating sheath on one side and the measurement electrode, the insulating spacer, and the upstream ground on the other side.

The downstream ground may then comprise an internal sheath comprising a cylindrical portion extending along the insulating sheath between the insulating sheath on one side and the ground electrode and the upstream ground on the other side.

BRIEF DESCRIPTION OF THE DRAWINGS

Other characteristics, objects, and advantages of the invention appear from the following description, which is purely illustrative and non-limiting, and which should be read with reference to the accompanying figures, in which:

FIG. 2 is a section view of such a system; and

Figure 1:
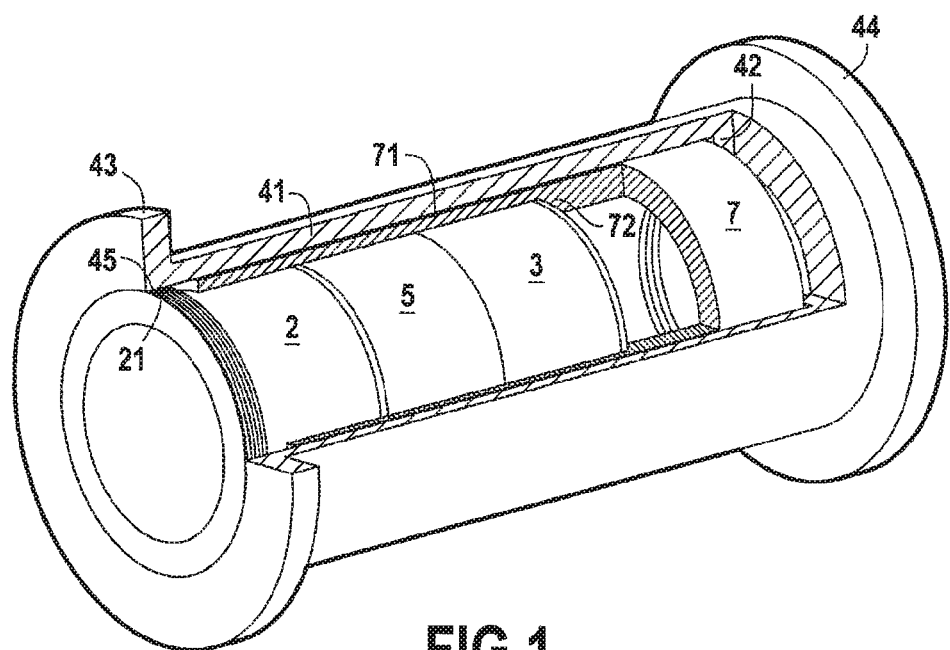
FIG. 1 is a fragmentary view of a system in an aspect of the invention.

In all of the figures, elements that are common are identified by reference numerals that are identical.

DETAILED DESCRIPTION OF EMBODIMENTS

FIGS. 1 and 2 are two views of a system in an aspect of the invention.

These figures show a system 1 for measuring variation in the gas content in a two-phase flow.

The system 1 as shown comprises an upstream ground 2, a measurement electrode 3, and a downstream ground 4 arranged in succession in an insulating sheath 6 (not shown in FIG. 1) that provides both thermal and electrical insulation.

The measurement electrode 3, the upstream ground 2, and the downstream ground 4 form a system of electrodes; the measurement electrode 3 typically forms the cathode, while the upstream ground 2 and the downstream ground 4 then form anodes.

The measurement electrode 3 is arranged in such a manner as to be separate from the upstream ground 2 so that the measurement electrode 3 and the upstream ground 2 are not in direct electrical contact.

Thus, by way of example, the system includes an insulating spacer 5 defining a minimum spacing between the measurement electrode 3 and the upstream ground 2.

The upstream ground 2, the insulating spacer 5, the measurement electrode 3, and the downstream ground 4 are each of identical inside section, so as to define an internal duct of constant section when they are arranged end to end, e.g. a tubular section giving a circular cylinder.

The upstream ground 2 and the downstream ground 4 are made of conductive material, and form the structure of a portion of a flow pipe for a two-phase fluid.

While the system is in use, the upstream ground 2 and the downstream ground 4 are thus connected directly to the electrical ground of the installation, as is the pipe in which the system is inserted.

The insulating spacer 5 is arranged between the upstream ground 2 and the measurement electrode 3; the insulating spacer 5 is made of an electrically insulating material so as to insulate them electrically from each other.

The measurement electrode 3 thus makes it possible to measure the permittivity of a two-phase fluid flowing in the internal duct formed in this way by the system 1, said two-phase fluid flowing from the upstream ground 2 towards the downstream ground 4, as indicated by arrows in FIG. 2.

Such a measurement of variation in permittivity makes it possible to detect variation in the content of gas within the two-phase fluid.

Specifically, the permittivity of a liquid medium varies in proportion to the gas content in the liquid. Thus, by electrically charging the upstream ground 2, it is possible to measure the potential of the measurement electrode, with variation in the measured capacitance difference then directly representing variation in the content of gas within the two-phase fluid flowing in the internal duct.

By way of example, the measurements taken in this way may be processed by means of a conditioning unit serving to convert the capacitance variation into variation of an electrical magnitude (voltage, current, frequency, . . . ), and may in particular be connected to a computer or to any other suitable processor unit.

Furthermore, by connecting the upstream ground 2 and the downstream ground 4 to the electrical ground of the installation, the proposed system 1 has reduced the sensitivity to interference, so the processing of the measurement is thereby simplified compared with conventional measurement systems in which the elements forming the anode and the cathode of the system 1 are electrically insulated from the pipe. Specifically, the proposed system uses the electrical ground of the installation as a reference electric potential, unlike prior systems for which each of the various electrodes is insulated from the pipe and thus from the ground of the installation.

The proposed system thus makes it possible to provide a capacitive sensor having at least one of is electrodes (in this example the upstream and downstream grounds 2 and 4 that typically form anodes) constituted by the pipe itself, and it is thus connected to the electrical ground of the pipe installation.

The system 1 is adapted to be incorporated in a two-phase flow line, e.g. a line for feeding a spacecraft with propellant. The system 1 is thus interposed between an upstream pipe and a downstream pipe, to which it is connected by means of flanges or connectors, for example.

The internal duct defined by the system 1 then has a section that is identical to the section of the upstream and downstream pipes to which it is to be connected.

The system 1 thus makes it possible to measure the variation in the content of gas within a two-phase flow, without generating head losses in the flow.

The various components of the system 1 are configured so as to be in line with the flow pipe and not within the flow, as is to be seen in known systems.

Furthermore, in the proposed system 1, the components taking the measurements and enabling variation in the content of gas within a two-phase flow to be measured are not themselves limited in terms of dimensions. The system 1 can thus be fitted to pipes of all dimensions, e.g. pipes having a diameter lying in the range 4 mm to 60 mm.

Furthermore, such a system 1 makes it possible to acquire data directly, without multiplexing, thereby considerably facilitating exploitation of the measurement compared with prior systems that generate multiplexed data.

Furthermore, in the event of the various electrodes presenting an internal section forming a circular cylinder, the measured response depends little on the radial position of air bubbles within the two-phase flow.

The system 1 also has a guard electrode 7 that is subjected to the same potential as the measurement electrode 3 in order to compensate the electrical disturbances caused in particular by the downstream ground 4 and by other mechanical elements of the system 1 connected to the upstream or downstream ground 2 or 4. The guard electrode 7 is then interposed between the measurement electrode 3 and the downstream ground 4, without being in contact either with the measurement electrode 3 or with the downstream ground 4.

In the embodiment shown in the figures, the guard electrode 7 comprises a guard sheath 71 presenting a cylindrical portion extending as far as the upstream ground 2, between the insulating sheath 1 on one side and the measurement electrode 3, the insulating spacer 5, and the upstream ground 2 on the other side, without making contact either with the measurement electrode 3 or with the upstream ground 2. The insulating spacer 5 can thus present an outside diameter that is perceptibly greater than the outside diameter of the measurement electrode 3 and of the upstream ground 2 so as to provide spacing between the guard electrode 7 and the measurement electrode 3 and upstream ground 2.

The downstream ground 4 presents an internal sheath 41 extending between the insulating sheath 6 on one side and the measurement electrode 3, the insulating spacer 5, the upstream ground 2, and the guard electrode 7, if any, on the other side.

As can be seen in the figures, the guard sheath 71 thus insulates the measurement electrode 3 and the spacer 5 from the downstream ground 4, the guard sheath 71 being interposed between the measurement electrode 3 and the spacer 5 on one side and the internal sheath 41 and the downstream ground 4 on the other side.

In the embodiment shown in the figures, the downstream ground 4 forms a downstream end of the system 1. The downstream ground 4 has a shoulder 42 from which the internal sheath 41 extends and that forms an abutment against which the guard electrode 7 is positioned.

In the same manner, the guard electrode 7 has a shoulder 72 from which the guard sheath 71 extends, the shoulder 72 forming an abutment against which the measurement electrode 3 is positioned.

In the embodiment shown in FIG. 2, the downstream ground 4 is initially positioned in the insulating sheath 6. Thereafter, the guard electrode 7 is inserted via the upstream end so as to come into abutment against the shoulder of the downstream ground 4. A sealing element 84 is typically arranged between the guard electrode 7 and the downstream ground 4 so as to insulate the guard electrode 7 electrically from the downstream ground 4.

The measurement electrode 3 is then inserted via the upstream end until it comes into abutment against the shoulder 72 of the guard electrode 71. A sealing element 87 is typically arranged between the guard electrode 7 of the downstream ground 4.

The spacer 5 is then inserted via the upstream end until it comes into abutment against the measurement electrode 3. Finally, the upstream ground 2 is inserted via the upstream end until it comes into abutment against the spacer 5. The spacer 5 typically includes centering means 52 and 53 so as to center the spacer 5 respectively relative to the upstream ground 2 and relative to the measurement electrode 3.

By way of example, the upstream ground 2 has a threaded portion 21 suitable for being screwed onto a threaded portion 45 of the internal sheath 41 of the downstream ground 4, e.g. forming the upstream end of the system 1.

By screwing the upstream ground 2 relative to the downstream ground 4 in this way, the upstream ground 2 serves to hold the various elements of the system 1 that are arranged between the upstream ground 2 and the downstream ground 4, i.e. the insulating spacer 5, the measurement electrode 3, and the guard electrode 7 in the embodiment shown.

In the embodiment shown, the downstream ground 4 presents two radial collars, one at each end, respectively an upstream collar 43 and a downstream collar 44.

The insulating sheath 6 is typically provided with a flange support 61 enabling the system 1 to be connected to a controller, for example, and comprising, by way of example, a leaktight and insulated coaxial connector 62 that is connected to the measurement and guard electrodes 3 and 7.

The coaxial connector 62 as shown in FIG. 2 comprises:
a core 63 connected to the measurement electrode 3;
a guard 64 arranged around the core 63 and connected to the guard electrode 7;
internal insulation 65 arranged between the core 63 and the guard 64; and
external insulation 66 arranged around the guard 64.

In operation, the potentials applied of the electrodes generate an electrostatic field.

It can readily be understood that the nature of the electrostatic field as generated in this way has an influence on the sensitivity of the measurements taken by the system 1.

Since the generated electrostatic field itself depends in particular on the dimensions of the various components and on their relative positions, the dimensions and the positions of the various components of the system 1 thus have an influence on the sensitivity of the system 1.

Figure 3:
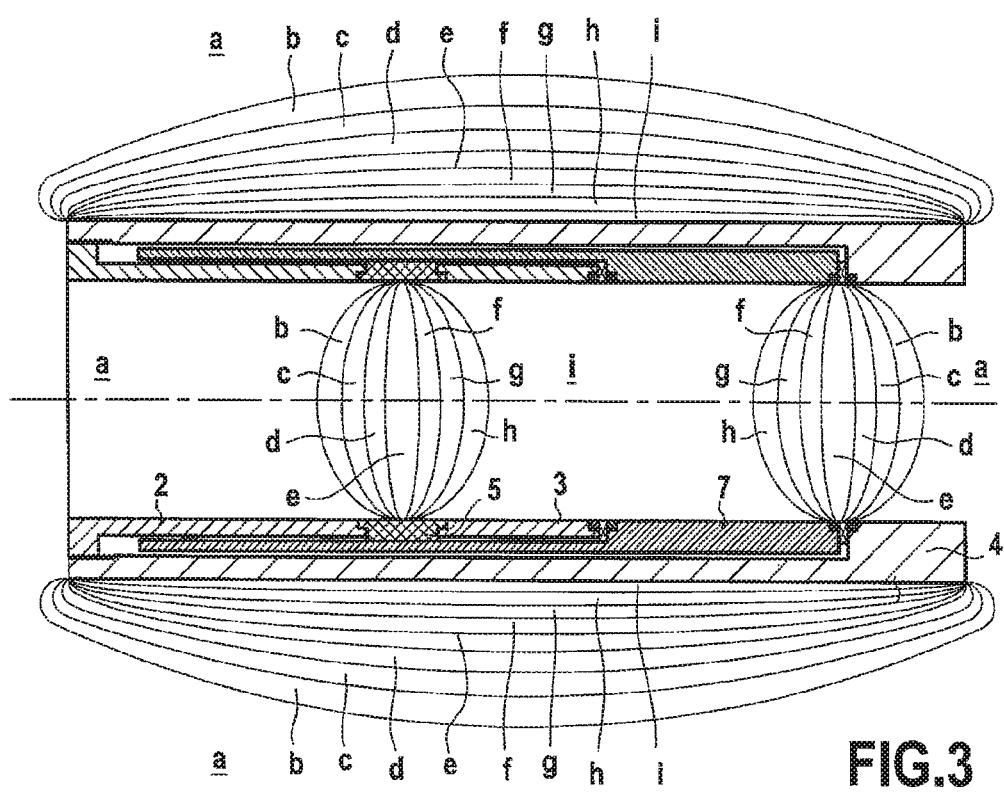
FIG. 3 is a diagram showing the field lines within such a system.

FIG. 3 shows the various elements of the system 1 as described above, together with the field lines that are generated while it is in operation.

The various values of the electrostatic field are designated by the letters a to i. The potential increases going from the letter a, which designates the lowest potential, to the letter i, which designates the highest potential.

As mentioned above, since permittivity variation is measured from the measurement electrode 3 over the portion of the system 1 that corresponds to the spacing between the measurement electrode 3 and the upstream ground 2, i.e. to the portion of the system corresponding to the insulating spacer 5 when the system 1 includes such an insulating spacer 5 between the measurement electrode 3 and the upstream ground 2. Consequently, in order to increase the sensitivity of the system 1, it is desired to have maximum variation of potential over this portion of the system 1.

Thus, the various components of the system are advantageously configured in such a manner that a maximum amount of field lines are situated within the portion of the system 1 corresponding to the gap between the measurement electrode 3 and the upstream ground 2, i.e. the portion of the system corresponding to the insulating spacer 5 when the system 1 includes such an insulating spacer 5 between the measurement electrode 3 and the upstream ground 2.

The measurement electrode 3 is typically arranged so as to be not very far away from the upstream ground 2, e.g. at a distance lying in the range 10 mm to 20 mm for a pipe having a diameter of 29 mm, or indeed a distance of about 15 mm. Consequently, the insulating spacer 5 is of a size that is adapted so as to guarantee this spacing.

In a particular embodiment, the measurement electrode 3 may be subdivided into a plurality of sectors, e.g. four sectors, each corresponding substantially to one-fourth of a circle when the flow is in a tubular pipe. By way of example, the various sectors may be insulated from one another by portions of insulating material.

The measurements performed on each of the sectors then make it possible to detect the sector in which the gas bubbles of the two-phase flow are situated, thus making it possible to determine the proportion of gas in the various sectors of the two-phase flow.

The invention claimed is:
1. An assembly comprising an upstream pipe, a downstream pipe, and a system for measuring variation in gas content within a two-phase flow, said system comprising:
an insulating sheath presenting an upstream end and a downstream end; and
an upstream ground, a measurement electrode, a guard electrode, and a downstream ground arranged in succession in said insulating sheath and each presenting an identical internal section defining an internal flow duct for a two-phase flow from the upstream ground towards the downstream ground, the guard electrode being configured so as to be subjected to the same potential as the measurement electrode, the measurement electrode being configured so as to measure the capacitance of the medium constituting the two-phase flow relative to the upstream ground, and to measure variation of that capacitance;
the assembly being characterized in that:
said upstream and downstream pipes present an internal section identical to the internal section of said measurement system;

said upstream and downstream pipes are in fluid flow connection with each other via the measurement system so that the internal duct of the measurement system extends the internal ducts of the upstream and downstream pipes; and the upstream ground and the downstream ground are electrically connected to the upstream pipe and to the downstream pipe, respectively;

said assembly further comprising a processor unit configured to process the capacitance measurements taken between the measurement electrode and the upstream ground, wherein each of the upstream ground and the downstream ground includes electrodes including a conductive material.

2. An assembly according to claim 1, further comprising an insulating spacer arranged in the insulating sheath between the measurement electrode and the upstream ground, the spacer presenting an internal section identical to that of the measurement electrode and of the upstream ground so as to insulate the upstream ground electrically from the measurement electrode.

3. An assembly according to claim 2, wherein said guard electrode comprises a guard sheath having a cylindrical portion extending to the upstream ground between the insulating sheath on one side and the measurement electrode, the insulating spacer, and the upstream ground on the other side.

4. An assembly according to claim 3, wherein the downstream ground comprises an internal sheath comprising a cylindrical portion extending along the insulating sheath between the insulating sheath on one side and the ground electrode and the upstream ground on the other side.

* * * * *